US00PP31024P2

(12) United States Plant Patent
Van Swieten

(10) Patent No.: US PP31,024 P2
(45) Date of Patent: Nov. 5, 2019

(54) ***PHALAENOPSIS* ORCHID PLANT NAMED 'PHALFUFLY'**

(50) Latin Name: ***Phalaenopsis* hybrid**
Varietal Denomination: PHALFUFLY

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,857

(22) Filed: May 8, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

(56) References Cited

PUBLICATIONS

Upov Pluto Plant Variety Database Apr. 11, 2019, retrieved on Apr. 22, 2019, retrieved from the Internet at www3.wipo.int/pluto/user/en/index.jsp, one page. (Year: 2019).*
EU Community Plant Variety Rights Application No. 2017/2398, Application n°A201702678, filed Sep. 28, 2017, 8 pages.
EU Community Plant Variety Office Official Gazette, Jun. 2017, Dec. 15, 2017, cover page and pp. 38, 59.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALFUFLY', particularly characterized by having small, red-purple flowers with white edges, small centers and red-purple lips, 1 to 3 peduncles that are short and sturdy, leaves that are oblong, and is propagated by meristem tissue culture, is disclosed.

3 Drawing Sheets

Genus and species: *Phalaenopsis* hybrid.
Variety denomination: 'PHALFUFLY'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFUFLY'.

The new *Phalaenopsis* plant is a product of a planned breeding program conducted by the inventor in Bleiswijk, The Netherlands. The objective of this breeding program was to create a new *Phalaenopsis* plant with numerous attractive and small, red-purple flowers with white edges, small centers, and red-purple lips, suitable for potted plant production.

The new *Phalaenopsis* plant 'PHALFUFLY' is a result of cross-pollination made by the inventor in March 2008 in Bleiswijk, The Netherlands of the proprietary female, or seed parent, *Phalaenopsis* hybrid '20413-03' (unpatented) with the proprietary male, or pollen parent, *Phalaenopsis* hybrid '01-1787' (unpatented).

The new *Phalaenopsis* was selected by the inventor as a single plant within the progeny of the stated cross-pollination in a controlled greenhouse in Bleiswijk, The Netherlands in April 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 28, 2017. 'PHALFUFLY' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFUFLY' as a new and distinct variety of *Phalaenopsis* plant.

1) Small, red-purple flowers with white edges, small centers and red-purple lips;
2) 1 to 3 peduncles;
3) Peduncle is short and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in March 2018. Colors in the photographs may differ from the color values cited in the detailed botanical description, which accurately describe the actual colors of the new variety.

DESCRIPTION OF THE NEW VARIETY

Figure 1:
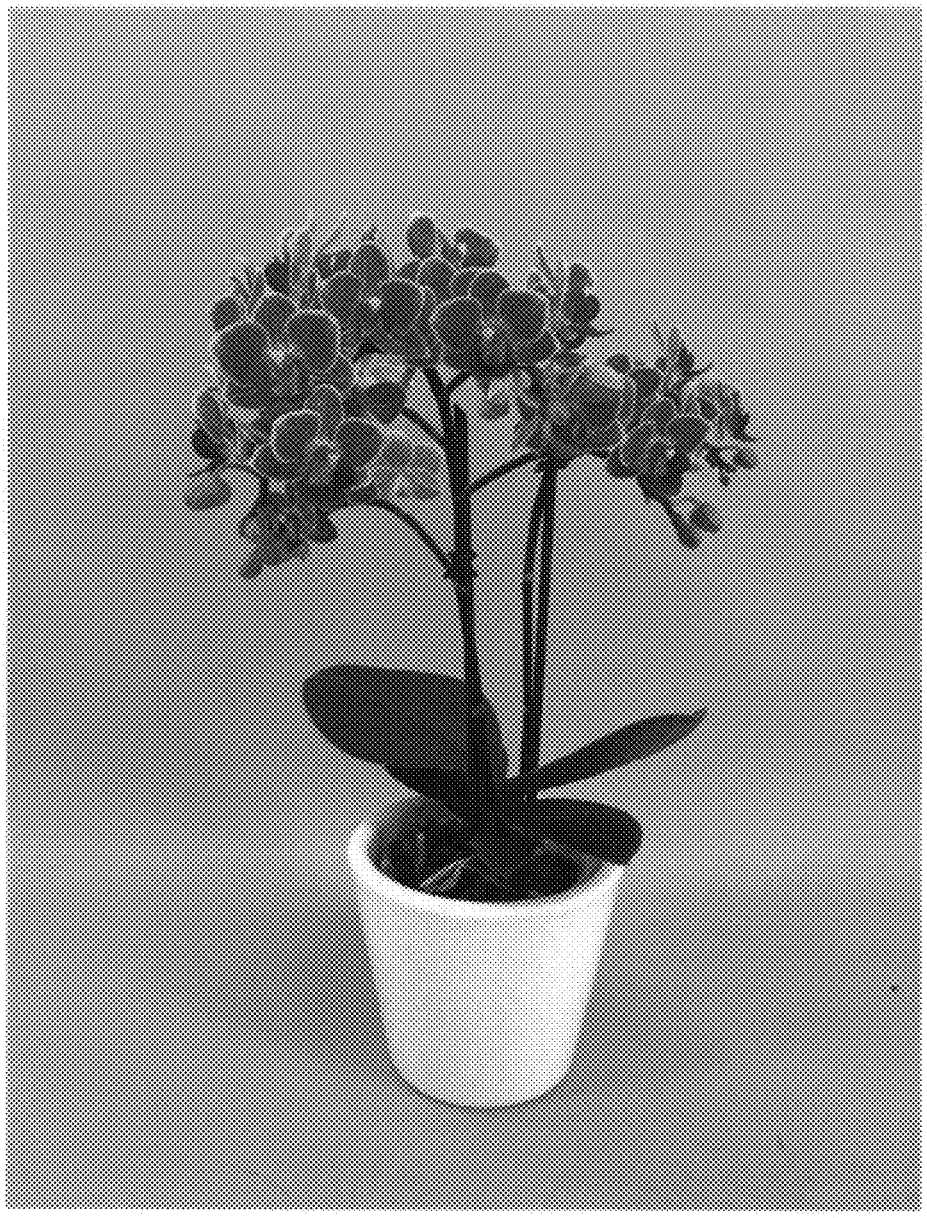
FIG. 1 shows the overall plant habit, including blooms, buds and foliage of 'PHALFUFLY'.
Figure 2:
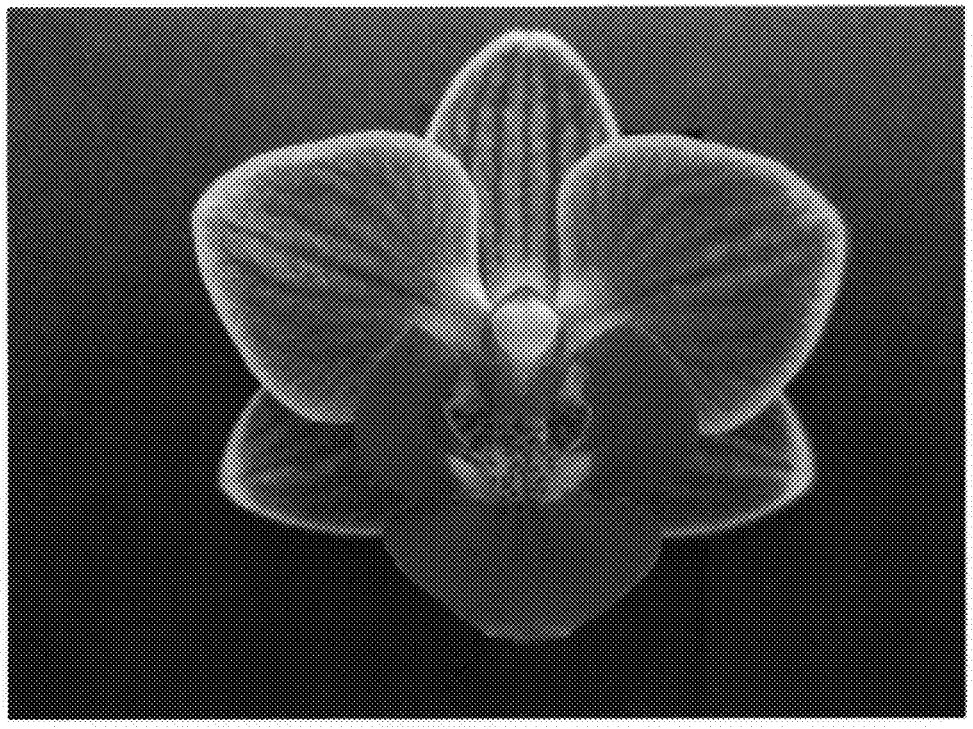
FIG. 2 shows a close-up of a flower of 'PHALFUFLY'.
Figure 3:
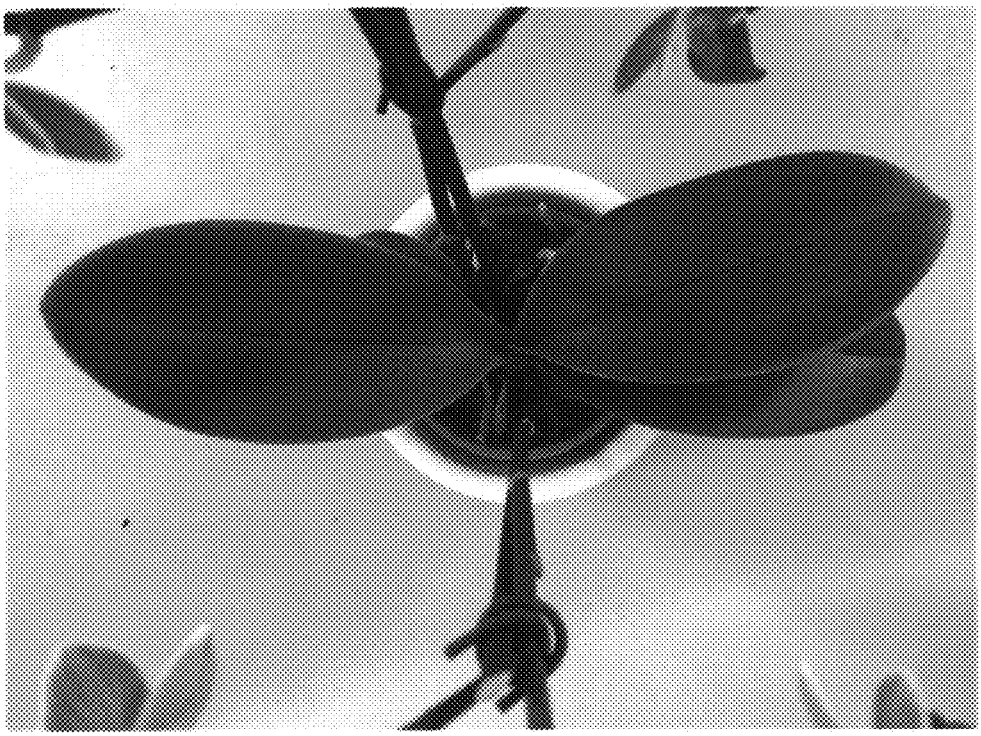
FIG. 3 shows an overhead view of the leaves of 'PHALFUFLY'.

The following detailed description sets forth the distinctive characteristics of 'PHALFUFLY'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in March 2018 on flowering plants which were planted in 9 centimeter (diameter) pots. After in-vitro propagation, the plants were grown in nursery trays for 18-20 weeks, followed by transplantation to 9 centimeter (diameter) pots and grown in a greenhouse between 27° C. to 29° C. for 25 weeks, continued by a cooling period of 6 weeks between 18° C. to 20° C. and 11 weeks in a greenhouse of 21° C. Flowering occurs after 42-weeks in a 9 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFUFLY'.

Parentage:

*Female parent*.—*Phalaenopsis* cultivar '20413-03' (unpatented).

*Male parent*.—*Phalaenopsis* cultivar '01-1787' (unpatented).

Propagation:

*Type*.—Meristem tissue culture.

Roots:

*Root description*.—Greyed-green colored roots (between RHS 190B and 190C) with branching lateral roots having light green (RHS 145D) colored root tips.

Plant:

*Commercial crop time to flowering*.—Following asexual propagation (in-vitro), the rooted cuttings grow for 18-20 weeks. After transplantation into 9 cm pots, the plants are finished after 40 to 42 weeks.

*Growth habit of peduncle*.—Standard, green leaves, panicle.

*Height* (*from soil level to top of inflorescence*).—Approximately 29.0 cm to 34.0 cm.

*Width* (*measured from leaf tips*).—About 22.0 cm to 24.0 cm.

*Vigor*.—Moderate.

Leaves:

*Mature leaves*.—Quantity per plant: 7 to 10 leaves are produced before flowering. Length (fully expanded): 12.0 cm to 13.0 cm. Width: 6.0 cm to 7.0 cm. Shape: Oblong. Base shape: Slightly to moderately elongated. Apex: Obtuse unequal. Leaf blade angle with the petiole (measured from the horizontal position): Between 20 degrees and 35 degrees. Leaf margin: Entire. Color: Upper surface: RHS 147A. Lower surface: RHS 147B. Texture (both upper and lower surfaces): Rough. Thickness: 2.6 mm to 2.9 mm. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—25 to 34.

*Length*.—29.0 cm to 34.0 cm.

*Diameter*.—4.1 mm to 4.5 mm.

*Strength*.—Moderate.

*Aspect*.—Upright to slightly pendant.

*Texture*.—Smooth.

*Color*.—Brown (RHS N200A).

*Internode length*.—3.0 cm to 5.0 cm.

Inflorescence description:

*Appearance*.—Upright to slightly pendant, panicle inflorescence with bilaterally symmetrical flowers that open in succession beginning with the lowermost flower.

*Average number of inflorescence per flowering stem*.—Around 20 flowers on a flowering stem, depending on growing conditions.

*Average number of individual flowers per inflorescence*.—30.

*Inflorescence size*.—Height (from base to tip): 180.0 mm to 210.0 mm.

*Flowering time*.—First flowers can be expected 7 to 8 months after planting in a 9 cm (diameter) pot.

*Flower*.—Height: 30.0 mm to 32.0 mm. Diameter: 35.0 mm to 40.0 mm. Depth of lip: 13.0 mm to 15.0 mm.

*Flower longevity*.—On the plant: 8 to 12 weeks.

*Fragrance*.—Absent.

*Flower bud*.—Average size: Small to medium. Length: 11.0 mm to 13.0 mm. Width: 9.0 mm to 11.0 mm. Shape: Egg shaped. Color: Light green (RHS 145D) at the base; purple-red (RHS N77D) and red-purple (RHS N78B) toward the tip.

*Petals*.—Arrangement: Open/free. Shape: Semi-circular. Apex: Obtuse asymmetric. Margin: Slightly undulated. Length (from base to tip): 15.0 mm to 17.0 mm. Width: 15.0 mm to 17.0 mm. Color (when fully opened): Upper surface: Basic color: Red-purple (RHS N78B). Over color: Red-purple (RHS N78A) stripes and white (RHS NN155C) edge. Stripes: Medium. Spots: None. Lower surface: Basic color: Purple-pink (between RHS N78C and N78D). Over color: White edge (RHS NN155C).

*Dorsal sepal*.—Shape: Elliptic. Apex: Rounded to slightly emarginated. Margin: Entire. Length (from base to tip): 18.0 mm to 20.0 mm. Width: 12.0 mm to 14.0 mm. Color (when fully opened): Upper surface: Basic color: Red-purple (RHS N78B). Over color: Red-purple (between RHS N78A and N78B) stripes and white (RHS NN155C) edge. Spots: None. Netting: None. Lower surface: Basic color: Red-purple (RHS N78B). Over color: White (RHS NN155C) edge and red-purple (RHS N78B) stripes.

*Lateral sepals*.—Shape: Ovate. Apex: Obtuse asymmetric. Margin: Entire. Length (from base to tip): 16.0 mm to 18.0 mm. Width: 13.0 mm to 15.0 mm. Color (when fully opened): Upper surface: Basic color: Red-purple (RHS N78B). Over color: Light green (RHS 145C) at the base; red-purple (between RHS N78A and N78B) stripes and white (RHS NN155C) edge. Spots: None. Netting: None. Lower surface: Basic color: Light red-purple (RHS N78D). Over color: Light green (RHS 145D) at the base and red-purple (RHS N78B) vein.

*Labellum* (*lip*).—Whiskers: Absent. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 11.0 mm to 13.0 mm. Width: 7.0 mm to 9.0 mm. Color: Upper surface: Slightly yellow (RHS 9A) at the base with few stripes of dark red (RHS 59A) ending in an edge of dark red (RHS 59A). Lower surface: White (RHS N155A) with dark red (RHS 59A) toward the front.

*Apical lobe*.—Shape: Ovate. Margin: Entire. Length: 13.0 mm to 15.0 mm. Width: 13.0 mm to 15.0 mm. Color: Upper surface: Slightly yellow (RHS 9A) at the base; dark red (RHS 59A) and red-purple (RHS N78A) toward the tip. Lower surface: White (RHS N155A) with yellow (RHS 9A) toward the front and red-purple edge (RHS N78A). Stripes: 3 small stripes (RHS 59A). Spots: None. Netting: Few.

*Callus*.—Average size: Small. Height: 2.0 mm to 3.0 mm. Length: 3.0 mm to 4.0 mm. Width: 1.0 mm to 2.0 mm. Color: Yellow (RHS 13B) dotted (RHS 59A).

Reproductive organs:

*Column*.—Length: 6.0 mm to 8.0 mm. Diameter: 3.8 mm to 4.1 mm. Color: Red-purple (RHS N78A). Anther cap color: White (RHS 155B).

*Pollinia*.—Quantity: 2. Diameter: 0.7 mm to 0.9 mm. Color: Orange (RHS 25A).

*Ovary*.—Length: 5.0 mm to 7.0 mm. Diameter: 1.3 mm to 1.5 mm.

*Pedicel*.—Length: 17.0 mm to 19.0 mm. Diameter: 1.5 mm to 1.7 mm. Color: Green (RHS 146A) at the base; light green (RHS 145D) and light purple (RHS 75A) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFUFLY' differs from female parent plant '20413-03' (unpatented) in that 'PHALFUFLY' has oblong shaped leaves and no whiskers, whereas '20413-03' has obovate shaped leaves and whiskers. Additionally, 'PHALFUFLY' has wider dorsal sepals than '20413-03'.

The male parent plant of 'PHALFUFLY', cultivar '01-1787', is no longer in existence, so a meaningful comparison cannot be made.

'PHALFUFLY' is most similar to the commercial *Phalaenopsis* plants named 'ANTAPHANEL' (unpatented) and 'PHALDONFI' (U.S. Plant Pat. No. 26,066). 'PHALFUFLY' differs from the commercial variety 'ANTAPHANEL' in that 'PHALFUFLY' has a concave flower shape in lateral view, ovate shaped apical lobes, and no whiskers, whereas 'ANTAPHANEL' has a flat flower shape in lateral view, triangular shaped apical lobes, and whiskers. Additionally, 'PHALFUFLY' has smaller flowers and shorter plants than 'ANTAPHANEL'.

'PHALFUFLY' differs from the commercial variety 'PHALDONFI' in that 'PHALFUFLY' has no whiskers, whereas 'PHALDONFI' has whiskers. Additionally, 'PHALFUFLY' has smaller flowers and shorter plants than 'PHALDONFI'.

I claim:

1. A new and distinct variety of *Phalaenopsis* plant named 'PHALFUFLY', substantially as described and illustrated herein.

* * * * *